United States Patent [19]

Brooke

[11] Patent Number: 4,886,492
[45] Date of Patent: Dec. 12, 1989

[54] SURGICAL SUCTION TIP WITH FILTER

[76] Inventor: Gerard M. Brooke, The Bannut Tree, New Inn Lane, Avening GL8 8NB, Gloucestershire, England

[21] Appl. No.: 169,854

[22] Filed: Mar. 18, 1988

[30] Foreign Application Priority Data

Mar. 24, 1987 [GB] United Kingdom ................. 8706958

[51] Int. Cl.⁴ ............................................ A61M 31/00
[52] U.S. Cl. ...................................... 604/49; 604/902
[58] Field of Search ......................... 604/902, 264, 48; 433/91-93; 210/448, 452

[56] References Cited

U.S. PATENT DOCUMENTS

| | | | |
|---|---|---|---|
| 1,693,741 | 12/1928 | Wuest ................................... | 210/448 |
| 3,317,043 | 5/1967 | Vanderpoel ......................... | 210/448 |
| 3,469,706 | 9/1969 | Kissel ................................... | 210/448 |
| 3,785,380 | 1/1974 | Brumfield ............................ | 604/902 |
| 4,468,217 | 8/1984 | Kuzmick et al. .................... | 604/902 |
| 4,654,141 | 3/1987 | Frentzel .............................. | 210/448 |

Primary Examiner—Jerome L. Kruter
Attorney, Agent, or Firm—Abelman Frayne Rezac & Schwab

[57] ABSTRACT

A surgical suction tip comprises a tubular body portion with a hollow tip portion at one end communicating into the body portion, and a cap portion releasably closing the other end, a tubular connecting portion mounted externally on the cap portion communicating through the cap portion into the body portion. A hollow filter member within the body portion defines an annular chamber between the filter member and the body portion and communicating with the tubular connecting portion through the cap portion, a plurality of apertures in the filter member connecting the interior of the filter member with the annular chamber. The body portion has locating means thereon locating one end of the filter member within the body portion, while the other end of the filter member is closed. Waste material flows from the tip portion into the hollow interior of the filter member and then to the annular chamber and to the tubular connecting portion.

4 Claims, 1 Drawing Sheet

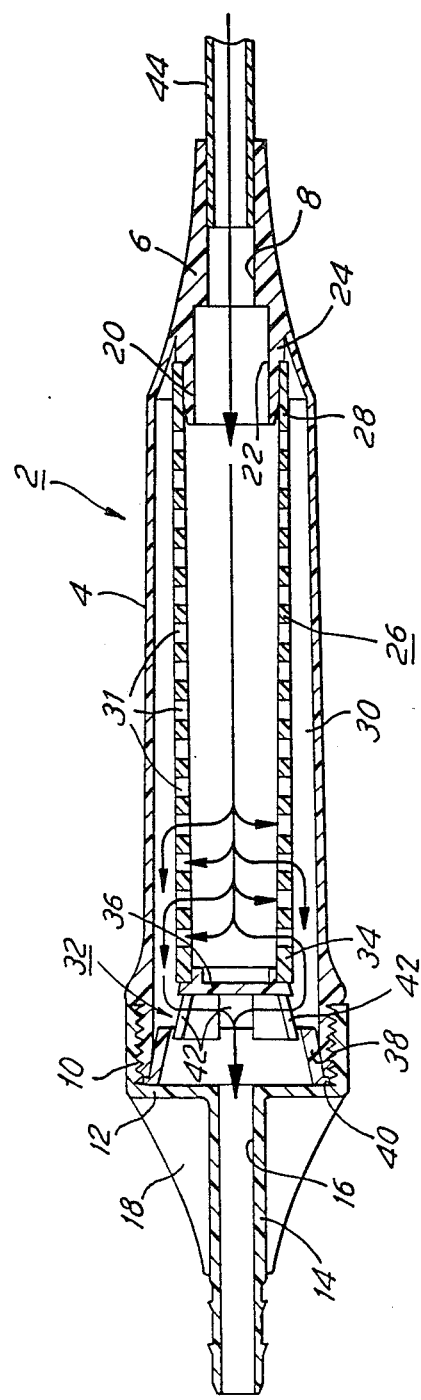

SURGICAL SUCTION TIP WITH FILTER

BACKGROUND OF THE INVENTION

The present invention relates to surgical suction tips such as are used to remove waste matter from the body during surgery.

In orthopaedic surgery, for example when replacing a hip joint, it is often necessary to clean out the centre of a bone, primarily the femur, prior to fitting the prosthesis, and it is common practice to utilise a suction tip and associated suction source to remove unwanted gelatinous blood, bone splinters, tissue and the like.

Such arrangements commonly comprise a suction source acting through a container and a length of tubing to the hand-held suction tip itself whereby solid and liquid waste are drawn through the suction tip, along the tubing and into the container.

However, the nature of the waste material so removed from a patient is such that the tip itself and the tubing therefrom are easily clogged by bits of tissue and other matter. It is then necessary to clean out the suction line or the suction tip before the operation can be continued and this is clearly a time-consuming and messy process.

It has been proposed to provide a surgical suction tip incorporating a removable filter element such as disclosed in U.S. Pat. No. 4468217. However, the filter unit itself is of relatively complex construction, embodying on it, as well as the filter element,, means for locating the input end of the filter element in position within the associated housing and closure means for enabling insertion and removal of the filter unit into and from the housing.

Furthermore, the waste material is drawn into an annular chamber within the housing before passing through the wall of the filter into the interior thereof and thence from the suction tip. Thus it will be appreciated that the solid matter of the waste material is retained within the annular chamber of the housing rather than in the filter element itself, and any clogging up of the suction tip requires not only removal and cleaning of the filter element but also cleaning out of the housing.

SUMMARY OF THE INVENTION

It would be desirable to be able to provide a surgical suction tip less likely to clog up and more easily cleaned than heretofore.

According to the present invention there is provided a surgical suction tip comprising a tubular body portion having a hollows, reduced-diameter tip portion at one end thereof the bore of which communicates into the interior of the body portion, a releasable cap portion closing the other end of the body portion and provided with a tubular connecting portion externally thereof the bore of which communicates through an aperture in the cap portion into the interior of the body portion, and a hollow filter member located within the body portion to define a chamber of generally annular transverse section between the filter member and the inner wall of the body portion, the filter member being provided with a plurality of apertures therein interconnecting the interior of the filter member with said annular chamber, characterised in that the body portion has integrally formed therein, adjacent the tip portion thereof, location means to receive thereon and locate one end of the filter member within the body portion such that material entering the body portion through the tip portion flows into the hollow interior of the filter member, the other end of the filter member being closed, and the annular chamber within the body portion being in communication with the tubular connecting portion by way of said aperture in the cap portion.

It will thus be appreciated that liquid and solid matter enter the surgical suction tip through the tip portion thereof and are drawn into the interior of the filter member. The liquid content thereof continues to flow through the apertures in the filter member into the annular chamber and thence through the tubular connecting portion for collection, while the solid matter is retained within the hollow interior of the filter member.

As soon as the filter member is blocked by the solid matter, it can readily be removed from the body portion, cleaned out and replaced for further use of the surgical suction tip.

Thus the surgical suction tip of the invention provides a controlled build-up of solid matter in a predetermined location combined with ready disposal of said matter quickly and with little mess.

Preferably the filter location means comprises a tubular member extending co-axially within the body portion, the bore thereof forming a continuation of the bore through the tip portion, the one end of the filter member being a push-fit over said tubular member.

The tubular member may be provided with a plurality of circumferentially-spaced, axially extending ribs on the outer wall thereof for abutment by the one end of the filter member to locate said filter member axially relative to the tubular member and therefore to the body portion.

Conveniently the filter member further comprises a removable end cap located in, to close, the other end of the filter member, said end cap including a tapering annular skirt portion the free end of which is gripped between the other end of the body portion and the cap portion to locate said end cap in an operative position within the body portion, a plurality of apertures through the skirt portion of the end cap interconnecting the annular chamber within the body portion with the tubular connecting portion by way of the aperture in the cap portion.

Preferably the cap portion is internally threaded to be a screw-fit on the correspondingly externally threaded other end of the body portion.

The surgical suction tip may be of a rigid transparent plastics material such as styrene acrylic nitrite, and may be provided with a plurality of tubular extension pieces of different shapes and lengths each of which is a friction push-fit into the free end of the tip portion thereof.

BRIEF DESCRIPTION OF THE DRAWING

The drawing is a longitudinal section through a surgical suction tip according to the invention.

DESCRIPTION OF THE PREFERRED EMBODIMENT

Referring to the drawing, the illustrated surgical suction tip comprises a tubular body portion indicated generally at 2 and including a cylindrical main extent 4 and a tapering tip portion 6 at one end thereof having a central bore 8 therethrough communicating into the interior of the main extent 4. The main extent 4 of the body portion 2 tapers slightly with its internal diameter increasing gradually from the one end thereof to the other end thereof.

The other end of the main extent 4 of the body portion 2 is externally threaded at 10 and is closed by means of an internally-threaded end cap 12. Said end cap 12 has integrally formed therewith an external, axially extending connecting tube 14 the bore 16 in which communicates through the end cap 12. A plurality of circumferentially-spaced strengthening fins 18 are provided between the connecting tube 14 and the end cap 12.

Integrally formed within the one end of the body portion 2 is a tubular locating sleeve 20 extending from the tip portion 6 into the main extent 4, the bore 22 of said locating sleeve 20 forming an axial continuation of the bore 8 of the tip portion 6 and interconnecting said bore 8 with the hollow interior of the main extent 4 of the body portion 2.

The free end of the sleeve 20 is chamferred, while a plurality of circumferentially spaced, axially extending ribs 24 are provided on the external surface of the sleeve 20 to terminate short of the free end of said sleeve 20.

The surgical tip further comprises a hollow filter element 26 of generally cylindrical shape, the filter element tapering slightly from one end to the other with the wider one end extent 28 being a push fit over the sleeve 20 to locate said element laterally in position within the body portion 2. The free end of the filter element 26 abuts the ends of the ribs 24 on the sleeve 20 to determine the axial operative position of the filter element 26 within the body portion 2.

In said operative position, the filter element 26 defines, together with the inner wall of the body portion 2, an annular chamber 30 within the body portion 2, a plurality of holes 31 through the cylindrical wall of the filter element 26 interconnecting the hollow interior of said filter element 26 with said annular chamber 30. The bore 8 of the tip portion 6 communicates into said hollow interior of the filter element 26 by way of the bore 22 in the tubular locating sleeve 20. The tapering natures of the main extent 4 of the body portion 2 and the filter element 26 are such that the transverse cross-section area of the annular chamber 30 increases in size from the one end of the main extent 4 to the other end thereof.

A cap portion indicated generally at 32 is a close push-fit into the narrower other end extent 34 of the filter element 26 such that an end wall 36 of the cap portion seals and closes said other end of the filter element 26.

Integrally formed with the end wall 36 of the cap portion 32 is an annular, outwardly-tapering skirt portion 38 the free end of which is provided with an annular flange 40 adapted to locate the cap portion in the open other end of the main extent of the body portion 2 and to be gripped in sealing engagement between the end cap 12 and the body portion 2 when the end cap 12 is screwed onto said body portion 2.

The skirt portion 38 is provided with a plurality, for example four, of circumferentially spaced apertures 42 therethrough to interconnect the annular chamber 30 within the body portion 2 with the bore 16 of the connecting tube 16.

Conveniently the surgical suction tip, including the filter element 26, is moulded from a rigid, translucent plastics material such as styrene acrylic nitrite, while the tip is provided with a plurality of relatively flexible tubular extension pieces of different lengths and shapes one end of each of which is adapted to be a close push fit in the free end of the tip portion 6 of the surgical suction tip. One such extension piece is shown at 44.

The described device operates as follows. A length of tubing attaching to the connecting tube 14 feeds to a container (not shown) to which is also connected a suction source whereby said source exerts a suction effect on the extension piece 44 located in the tip portion 6 of the surgical tip.

Thus extraneous waste material adjacent the free end of the extension piece 44 is drawn into the surgical tip along paths defined by the arrows in the drawing, through the length of tubing connected to the tube 14 and is collected in the container.

Clearly the liquid content of said waste matter can pass through the holes 31 in the filter element 26 and can be drawn into the container. However, gelatinous or solid matter such as bone spliters, tissue and the like, which heretofore have been prone to clogging up established suction tip systems, cannot pass through the holes 31 and are therefore collected within the hollow interior of the filter element 26, the build-up of such matter beginning at the other end of the filter element 26 adjacent the end wall 36 of the cap portion 32 and continuing along the filter element 26 towards the one end thereof.

Once the filter element is itself substantially full of waste matter and liquid flow therethrough is substantially prevented, the end cap 12 is unscrewed from the body portion 2, the filter element 26 and attached cap portion 32 are withdrawn therefrom, the cap portion 32 is removed from the filter element 26 and the filter element is cleaned out.

Assembly of the surgical tip is the reverse of the above procedure, with the sleeve 20 serving to guide the filter element 26 onto its operative position within the body portion 2.

Thus it will be appreciated that a surgical suction tip according to the invention encourages blocking thereof but in a controlled manner and in a predetermined location, and whereby unblocking of the system can be effected quickly and with little mess, requiring only removal, cleaning and replacement of the filter element 26.

What I claim and desire to secure by Letters Patent is:

1. A surgical suction tip comprising a tubular body portion having an inner wall surface, a hollow, reduced-diameter tip portion at one end of said body portion and defining therein a bore which communicates into the interior of the body portion, a releasable cap portion closing the other end of the body portion and having an aperture formed therethrough, a tubular connecting portion provided externally of said cap portion into the interior of the body portion and defining therein a bore which communicates through the aperture in the cap into the interior of the body portion, a hollow filter member located within the body portion to define a chamber of generally annular transverse section between the filter member and the inner wall surface of the body portion, the filter member being provided with a plurality of apertures therein interconnecting the interior of the filter member with said annular chamber, and location means integrally formed within the body portion adjacent the tip portion thereof to receive thereon and to locate one end of the filter member within the body portion such that material entering the body portion through the tip portion flows into the hollow interior of the filter member, the other end of the filter member being closed, the annular chamber within the body portion being in communication with the tubular connecting portion by way of said aperture in the cap portion, in which said filter member further comprises a removable end cap located in, to close, the other end of the filter member, said end cap including a tapering annular skirt portion having a free end which is gripped between the other end of the body portion and the cap portion to locate said end cap in an operative position within the body portion, the skirt portion of the end cap defining therein a plurality of apertures which interconnect the annular chamber within the body portion with the tubular connecting portion by way of the aperture in the cap portion.

2. A surgical suction tip as claimed in claim 1 in which the filter location means comprises a tubular member extending coaxially which the body portion, said tubular member defining therein a bore which forms a continuation of the bore through the tip portion, the one end of the filter member being a push-fit over said tubular member.

3. A surgical suction tip as claimed in claim 2 in which the tubular member has an outer wall, a plurality of circumferentially-spaced, axially extending ribs being provided on said outer wall of the tubular member for abutment by the one end of the filter member to locate said filter member axially relative to the tubular member and therefore to the body portion.

4. A surgical suction tip as claimed in claim 1 and including an internal thread on the cap portion and a corresponding external thread on other end of the body portion whereby the cap portion is a screw-fit on said other end of the body portion.

* * * * *